US005857456A

United States Patent [19]

Sun et al.

[11] Patent Number: 5,857,456

[45] Date of Patent: Jan. 12, 1999

[54] INHALER APPARATUS WITH AN ELECTRONIC MEANS FOR ENHANCED RELEASE OF DRY POWDERS

[75] Inventors: Hoi Cheong Steve Sun, Plainsboro; Bawa Singh, Voorhees; Howard Christopher Rivenburg, Princeton; Pabitra Datta, West Windsor; Nitin Vithabhi Desai, Princeton Jct, all of N.J.

[73] Assignee: Sarnoff Corporation, Princeton, N.J.

[21] Appl. No.: 661,212

[22] Filed: Jun. 10, 1996

[51] Int. Cl.$^6$ .................... A61M 15/00

[52] U.S. Cl. .................... 128/203.15; 128/203.12

[58] Field of Search .................... 128/203.15, 203.12, 128/203.19; 239/3; 399/274; 118/688, 629; 347/127; 424/468

[56] References Cited

U.S. PATENT DOCUMENTS

| | | | |
|---|---|---|---|
| 3,611,982 | 10/1971 | Coriale | 118/688 |
| 3,831,606 | 8/1974 | Damani | 128/266 |
| 3,971,377 | 7/1976 | Damani | 128/266 |
| 4,047,525 | 9/1977 | Kulessa et al. | 128/208 |
| 4,072,129 | 2/1978 | Bright et al. | 118/629 |
| 4,160,257 | 7/1979 | Carrish | 346/159 |
| 4,197,289 | 4/1980 | Sturzenegger et al. | 424/21 |

(List continued on next page.)

FOREIGN PATENT DOCUMENTS

| | | |
|---|---|---|
| 0 129 985 A1 | 1/1985 | European Pat. Off. . |
| 2 064 334 | 6/1981 | United Kingdom . |
| 2 242 134 | 9/1991 | United Kingdom . |
| 2 274 273 | 7/1994 | United Kingdom . |
| WO 93/09832 | 5/1993 | WIPO . |
| WO 93/24186 | 9/1993 | WIPO . |
| WO 94/06497 | 3/1994 | WIPO . |
| WO 94/08552 | 4/1994 | WIPO . |
| WO 94/13271 | 6/1994 | WIPO . |
| WO 94/23772 | 10/1994 | WIPO . |
| WO 95/00127 | 1/1995 | WIPO . |

OTHER PUBLICATIONS

Donald A. Seanor, Triboelectrification of Polymers in K.C. Frisch and A. Patsis, Electrical Properties of Polymers (Technomic Publications, Westport, CT) pp. 37–58.

Toshiya Watanabe et al., Electrostatic Force and Absorption Current of Alumina Electrostatic Chuck, Jpn. J. Appl. Phys. vol. 31, pp. 2145–2150 (1992).

Larry D. Harsough, Electrostatic Wafer Holding, Solid State Technology, pp. 87–90 (Jan. 1993).

John Field, Electrostatic Wafer Clamping for Next–Generation Manufacturing, Solid State Technology, pp. 91–98 (Sep. 1994).

(List continued on next page.)

*Primary Examiner*—John G. Weiss
*Assistant Examiner*—V. Srivatava
*Attorney, Agent, or Firm*—William J. Burke

[57] ABSTRACT

The present invention is directed, in part, to an inhaler apparatus with a substrate having medicament deposited thereon, the substrate being configured for electronic release of the medicament. In preferred embodiments, the inhaler comprises a conductive layer and a dielectric layer thereon. In preferred embodiments, the inhaler further comprises a second conductive layer positioned above the substrate without having contact with the substrate. In certain preferred embodiments, the voltage source is connected to the conductive layer in the substrate and the second conductive layer above the substrate. In other preferred embodiments, the inhaler apparatus further comprises a third conductive layer positioned below the substrate, and the voltage source is preferably connected to the second conductive layer above the substrate and the third conductive layer below the substrate In another aspect, the present invention provides a method for dispensing a medicant from an inhaler, comprising: (a) providing an inhaler with a substrate having a medicant deposited thereon, the substrate comprising a conductive layer and a dielectric layer and a voltage source connected to said conductive layer; and (b) actuating the voltage source.

28 Claims, 2 Drawing Sheets

U.S. PATENT DOCUMENTS

| | | | |
|---|---|---|---|
| 4,332,789 | 6/1982 | Mlodozeniec | 424/27 |
| 4,353,365 | 10/1982 | Hallworth et al. | 128/203.15 |
| 4,564,285 | 1/1986 | Yasuda et al. | 399/274 |
| 4,570,630 | 2/1986 | Elliott et al. | 128/203.15 |
| 4,627,432 | 12/1986 | Newell et al. | 128/203.15 |
| 4,664,107 | 5/1987 | Wass | 128/200.23 |
| 4,685,620 | 8/1987 | Law et al. | 239/3 |
| 4,778,054 | 10/1988 | Newell et al. | 206/531 |
| 4,795,644 | 1/1989 | Zentner | 424/468 |
| 4,811,731 | 3/1989 | Newell et al. | 128/203.15 |
| 4,889,114 | 12/1989 | Kladders | 128/203.15 |
| 4,917,978 | 4/1990 | Ritt et al. | 430/23 |
| 4,921,727 | 5/1990 | Datta et al. | 427/57 |
| 4,921,767 | 5/1990 | Datta et al. | 430/23 |
| 4,971,257 | 11/1990 | Birge | 239/708 |
| 5,028,501 | 7/1991 | Ritt et al. | 430/23 |
| 5,031,610 | 7/1991 | Armstrong et al. | 128/200.23 |
| 5,035,237 | 7/1991 | Newell et al. | 128/203.15 |
| 5,115,803 | 5/1992 | Sioutas | 128/200.23 |
| 5,161,524 | 11/1992 | Evans | 128/203.15 |
| 5,176,132 | 1/1993 | Drought et al. | 128/203.15 |
| 5,192,548 | 3/1993 | Velasquez et al. | 128/203.12 |
| 5,239,993 | 8/1993 | Evans | 128/203.15 |
| 5,243,970 | 9/1993 | Ambrosio et al. | 128/203.15 |
| 5,263,475 | 11/1993 | Altermatt et al. | 128/203.15 |
| 5,278,588 | 1/1994 | Kubelik | 346/159 |
| 5,301,666 | 4/1994 | Lerk et al. | 128/203.15 |
| 5,327,883 | 7/1994 | Williams et al. | 128/203.12 |
| 5,415,162 | 5/1995 | Casper et al. | 128/203.12 |
| 5,619,984 | 4/1997 | Hodson et al. | 128/203.15 |
| 5,642,727 | 7/1997 | Datta et al. | 128/203.12 |
| 5,647,347 | 7/1997 | Van Oort | 128/203.15 |

OTHER PUBLICATIONS

J. –F. Daviet et al., Electrostatic Clamping Applied to Semiconductor Plasma Processing, I. Theoretical Modeling, J. Electrochem. Soc., vol. 140, No. 11, pp. 3245–3256 (Nov. 1993).

J. –F. Daviet et al., Electrostatic Clamping Applied to Semiconductor Plasma Processing, II. Experimental Results, J. Electrochem. Soc., vol. 140, No. 11, pp. 3256–3261 (Nov. 1993).

Peter Singer, Electrostatic Chucks in Wafer Processing, Semiconductor International, pp. 57–64 (Apr. 1995).

T. Watanabe, et al., Electrostatic Charge Distribution in the Dielectric layer of Alumina Electrostatic Chuck, Journal of Materials Science, vol. 29, pp. 3510–3616 (1994).

Mamoru Nakasuji et al., Low Voltage and High Speed Operating Electrostatic Wafer Chuck Using Sputtered Tantalum Oxide Membrane, J. Vac. Sci. Technol. A 12(5) pp. 2834–2839 (Sep./Oct. 1994).

Derwent Search Report (dated: May 20, 1996).

INHALER APPARATUS WITH AN ELECTRONIC MEANS FOR ENHANCED RELEASE OF DRY POWDERS

RELATED CO-PENDING U.S. PATENT APPLICATIONS

Related co-pending U.S. patent applications, Ser. Nos. 08/661,213 ("Inhaler Apparatus with Modified Surfaces for Enhanced Release of Dry Powders," filed simultaneously herewith), 08/630,049 ("Acoustic Dispenser," filed Apr. 9, 1996, and its continuation-in-part filed simultaneously herewith), 08/630,050 ("Electrostatic Chucks," filed Apr. 9, 1996) and its continuation-in-part, filed simultaneously herewith, 08/630,012 ("Chucks and Methods for Positioning Multiple Objects on a Substrate," filed Apr. 9, 1996), 08/471,889 ("Methods and Apparatus for Electronically Depositing a Medicament Powder Upon Predefined Regions of a Substrate," filed Jun. 6, 1995, and continuation-in-part thereof filed Jun. 6, 1996), 08/467,647 ("Apparatus for Electrostatically Depositing and Retaining Materials Upon a Substrate," filed Jun. 6, 1995) and 08/506,703 ("Inhaler Apparatus Using a Tribo-Electric Charging Technique," filed Jul. 25, 1995) describe, inter alia, the electrostatic deposition of objects, such as particles of powder, on a substrate, such as an inhaler substrate. The foregoing patent applications are hereby incorporated herein by reference, in their entirety.

The present invention is directed, in part, to an inhaler apparatus with a substrate having medicament deposited thereon, the substrate being configured for electronic release of the medicament. In another aspect, the present invention provides a method for dispensing a medicant from an inhaler, comprising: (a) providing an inhaler with a substrate having a medicant deposited thereon, the substrate comprising a conductive layer and a dielectric layer and a voltage source connected to said conductive layer; and (b) actuating the voltage source.

Numerous approaches have been taken in the design and manufacture of dry powder inhalers. For example, WO 93/09832 discloses an inhalation device having an elongate carrier of medicament powder, the medicament powder being released after impact from a hammer, the inhalation device having a convoluted channel to deagglomerate the medicament powder.

The disadvantages of the inhalers of the prior art include, for example, the inability of a patient suffering from a respiratory disorder, such as asthma, to inhale with sufficient force to receive an entire dosage. For example, a patient may only be able to generate an air flow rate of about 15 liters per minute. In most dry powder inhalers, the patient's inhalation supplies the energy required to dispense the medicament from the inhaler. The air flow rate generated by the patient's lungs significantly affects the amount of medicament that ultimately exits the inhaler and reaches the lungs.

Another disadvantage of the inhalers of the prior art includes the inability to accurately determine the amount of medicament dispensed, since the inhaler may dispense a greater or lesser amount of medicament, depending upon the patient's air flow rate, for example.

A further disadvantage of the inhalers of the prior art is a problem of agglomeration of the medicament powder. Agglomerated particles generally impact the mouth and throat rather than remaining in the air flow for deposition on the lungs. One of the approaches to remedying this problem has been the provision of tortuous channels in the inhalers of the prior art to promote deagglomeration. This approach suffers from drawbacks, however, such as the deposition of the medicament along the channels, thereby leading to inaccurate dosage dispensing.

Another disadvantage encountered in the inhalers of the prior art is unintended dislodging, in which the medicament is discharged, for example, upon dropping the inhaler.

For the foregoing reasons, there is a need for a dry powder inhaler capable of delivering an accurate unit dosage of medicament at a low flow rate, such as 15 liters per minute, yet which substantially retains the medicament upon impact, such as dropping the inhaler.

SUMMARY OF THE INVENTION

The present invention is directed, in part, to an inhaler apparatus comprising a substrate with a medicant deposited thereon, the substrate comprising a conductive layer and a dielectric layer thereon. In certain embodiments, the conductive layer comprises at least one wire embedded in the substrate, and in other embodiments, the conductive layer in the substrate has openings therein, such as a mesh. Preferably, the conductive layer is connected to a voltage source. Further, in certain preferred embodiments, the conductive layer comprises at least one floating electrode, and the medicant is preferably deposited on the substrate in a pattern determined by the floating electrodes.

In preferred embodiments, the inhaler further comprises a second conductive layer positioned above the substrate without having contact with the substrate. Preferably, the second conductive layer has openings therein, and more preferably, the openings of the second conductive layer have a diameter of about 1.5 times the average diameter of the particles of medicant. In certain preferred embodiments, the voltage source is connected to the conductive layer in the substrate and the second conductive layer above the substrate. Preferably, the openings in the conductive layer in the substrate, when present, have a diameter approximately equal to the diameter of the openings in the second conductive layer above the substrate. Preferably, the openings of the second conductive layer have a diameter of about 1.5 times the average diameter of the particles of medicant.

In other preferred embodiments, the inhaler apparatus further comprises a third conductive layer positioned below the substrate, and the voltage source is preferably connected to the second conductive layer above the substrate and the third conductive layer below the substrate.

In another aspect, the present invention provides a method for dispensing a medicant from an inhaler, comprising:

(a) providing an inhaler with a substrate having a medicant deposited thereon, said substrate comprising a conductive layer and a dielectric layer and a voltage source connected to said conductive layer; and (b) actuating the voltage source.

Preferably, the voltage source is actuated substantially simultaneously with air flow, and the actuation is preferably a pulse having a duration of about 300 microseconds to about 1 millisecond. The voltage used is preferably from about 500 to about 2000 volts.

DETAILED DESCRIPTION OF THE INVENTION

Figure 4:
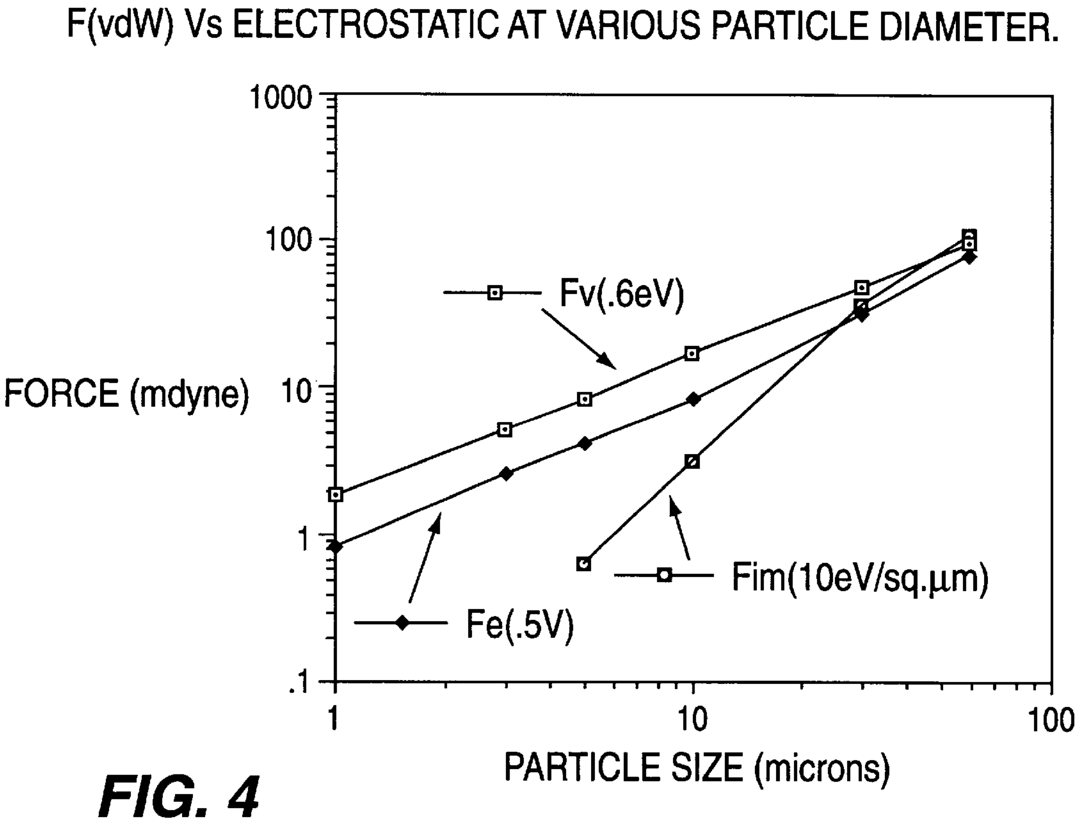
FIG. 4 is a graphical representation of 3 forces that adhere particles to the substrate of the inhaler; electrostatic forces ("Fe"), charge imaging forces ("Fim") and van der Waals forces ("Fv").

After depositing a powder onto a substrate of an inhaler, the powder is preferably accurately released upon inhalation by a patient. One of the obstacles to overcome is the adherence of the powder particles to the substrate. One of the forces holding the particles onto the substrate is a van der Waals force. Another holding force is the electrostatic force. A third holding force is a charge image force, generated by the charge of the powder particle in the local area of the substrate upon which it is adhered. These forces vary in magnitude depending upon, for example, the conductivity of the substrate. The van der Waals attraction increases over time, and the rate of increase is related to the rate of particle deformation due to greater contact area. See, for example, FIG. 4, which is a graphical representation of mathematical calculations of the foregoing forces, and which shows that these forces increase as the particle size increases.

The above-described problems are addressed, among others, by the current invention. In one aspect, the present invention provides for inhalers with an electronic means for enhanced release of dry powders.

The electronic means for enhancing release is provided in preferred embodiments of the invention by a substrate of the inhaler comprising a conductive layer and a dielectric layer, the dielectric layer having contact with the powder deposited thereon, Preferably, the dielectric layer is sufficiently thick to prevent the substrate from adhering the powder too tightly, but also will prevent the powder from releasing prematurely, such as due to the force of impact if the inhaler is dropped.

For example, in order for a powder particle having a charge:mass ratio of q/m on a dielectric layer having a thickness d and dielectric constant $\in_r$ to withstand a force of 500×gravity, $\in_o$ being the dielectric constant of free space, and ignoring the van der Waals attraction, the following equation applies:

$$500\times g \leq \frac{(g/m)^2 m}{4\pi\epsilon_o\epsilon_r d^2}$$

Assuming, for example, that q/m=30 $\mu$C/g, m=7 pg and $\in_r$=2, d can be as large as 76 $\mu$m. In reality, the holding force will be stronger than 500×g due to the van der Waals attraction. The above equation can be used as a general guideline in determining the preferred thickness of the dielectric layer of the substrate.

The inhaler substrate is preferably modified to minimize the surface area of the contact between the particles of the powder and the surface of the substrate, for those particles having a selected size. Particles having the desired size will have minimal contact with the substrate, and will therefore be more likely to be released from the substrate. In addition to making it more likely to release the desired particles, the modified substrate can be configured so that particles having an undesirable size are trapped. For example, if the surface area of contact between the particle and the substrate is high, such as with a particle having a size below the selected size, the higher contact leads to trapping the particle on the substrate rather than releasing it.

The minimization of the area of contact is preferably accomplished in the following ways. The surface area of contact can be minimized, for example, by providing indentations in the plane of the surface, or by providing raised areas in the plane of the surface. In preferred embodiments of the invention, at least one interior surface of the inhaler has indentations or raised areas with valleys therebetween, or other surface modification for decreasing the area of contact between the selected medicament particles and the interior surface of the inhaler in contact with the medicament. The contact of the medicament with the surface can occur, for example, before inhalation or during inhalation, such as contact with the substrate during deposition before inhalation, or contact with an interior surface of the mouthpiece during inhalation. Preferably, both the surface of the substrate upon which medicament is deposited and the mouthpiece and any other surfaces having contact with the medicament have indentations or raised areas therein, or any other surface structure for decreasing the area of contact between the selected medicament and the surface.

The indentation or raised area may be, for example, linear, tortuous, curved, circular, or any other desired configuration. In certain preferred embodiments, the indentations are in the form of linear grooves, which provides, for example, for ease of manufacturing.

The width of the indentation or the valley between two raised areas is preferably slightly smaller than the diameter of the smallest particle selected to be released, such as about 5% to about 20% smaller, and more preferably, about 10% to about 20% smaller. For example, if the particles to be released from the inhaler have a selected size of about 2 to about 6 microns, the width of the indentation or valley will preferably be about 1.8 microns. Preferably, the diameter of the indentation or valley is less than the diameter of the minimum respirable medicament particle size. For example, the pitch of the substrate, measured from the center of a valley to the center of a raised area, is preferably about 1 to about 2.5 microns for dispensing particles from about 2 to about 6 microns. Particle size can be determined, for example, using scanning electron microscopy.

The substrate of the inhaler has powder deposited thereon which is released upon inhalation. One means of powder deposition is ion printing, such as the technique described in Ser. No. 08/471,889. Preferably, however, the substrate is not pre-charged prior to deposition of the medicament powder to attract the powder to the substrate. Instead, an electrostatic chuck is preferably used to electrostatically attract charged powder for deposition. For example, in certain preferred embodiments, the substrate itself forms an electrostatic chuck. Specifically, the conductive layer of the substrate has the configuration of an electrostatic chuck with floating electrodes for charge imaging, described in co-pending patent application Ser. No. 08/630,050 (entitled "Electrostatic Chucks," filed Apr. 9, 1996) which is incorporated herein in its entirety. The powder can be deposited on the substrate using an acoustic dispenser described in co-pending patent application Ser. No. 08/630,049 (entitled "Acoustic Dispenser," filed Apr. 9, 1996) which is also hereby incorporated herein by reference, in its entirety.

Briefly, an electrostatic chuck for charge imaging comprises three layers, preferably with an optional fourth layer. The bottom layer is the lower conductive layer, which is also known as the backing electrode. The second layer, on top of the lower conductive layer, is a dielectric layer. The third layer is an upper conductive layer on top of the dielectric layer, and this upper conductive layer has two types of electrodes, floating electrodes and shielding electrodes. In preferred embodiments, the floating electrodes are electrically isolated from the other conductors, and there is a gap between the floating and shielding electrodes. The fourth layer, on top of the upper conductive layer, is a dielectric layer, which is preferably the layer having contact with the medicament powder, the thickness of this layer being the subject of the above mathematical formula. Preferably, this layer is made of polyimide or another material of high dielectric strength. Without being limited to a particular theory, it is believed that when a potential is applied across the shielding and backing electrodes, a charge redistribution occurs on the floating electrodes. This charge redistribution causes electrostatically charged objects to be attracted to the areas of the chuck corresponding to the floating electrodes, thus resulting in deposition in these areas. Preferably, there is a high fringing field in the gap between the floating and shielding electrodes, but this field is preferably not large enough to cause electrical discharge.

Figure 5:
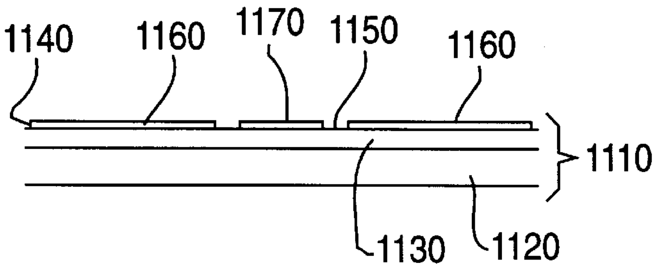
FIG. 5 is a cross-sectional schematic view of an electrostatic chuck with floating electrodes on the upper conductive layer for charge imaging.
Figure 6:
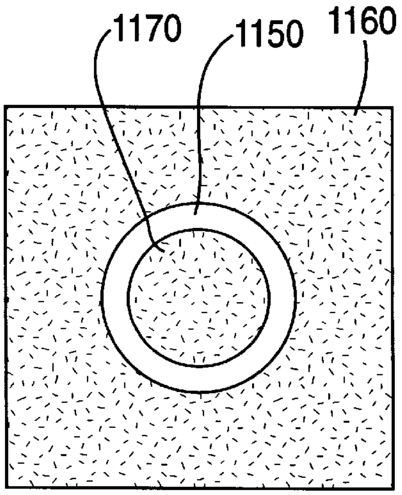
FIG. 6 is a top view of a floating electrode of FIG. 5.

See, for example, FIG. 5, which is a cross-sectional schematic view of an electrostatic chuck with floating electrodes on the upper conductive layer for charge imaging, FIG. 6, which is a top view of a floating electrode of FIG. 5 See also co-pending application U.S. Ser. No. 08/630,050 "Electrostatic Chucks"), filed Apr. 9, 1996, a continuation-in-part of which has been filed simultaneously herewith. Referring to FIG. 5, for example, the chuck 1110 has a lower conductive layer 1120, with a dielectric layer 1130 on top of it. The dielectric layer has an upper conductive layer 1140 on top of it. The upper conductive layer 1140 is electrically connected, but with a gap 1150 between a shielding electrode 160 and a floating electrode 1170. A top view of the upper conductive layer 1140 is shown in FIG. 6, with the floating electrode 1170 in the center, and a gap 1150 between the floating electrode and the surrounding shielding electrode 1160. During use, a bias potential is applied between the shielding electrode and the lower conductive layer. If the particles to be deposited are positively charged, the bias potential will be negative, and if the particles to be deposited are negatively charged, the bias potential will be positive. Preferably, the shielding electrode is connected to ground. During deposition of the particles, the length of time of the deposition will preferably be continued until each and every floating electrode has reached its limit in which the potential of the floating electrode matches the potential of the shielding electrode.

Using an electrostatic chuck with floating electrodes to deposit powder onto a substrate, the amount of powder deposited on the substrate is determined by the charge or bias potential of the chuck, and only a finite amount of powder can be deposited. Without being limited to a particular theory, it is believed that the deposition of powder ends when the charges on the floating electrode can no longer be redistributed, which occurs when the shielding electrode and the floating electrode have substantially the same potential. Preferably, both the floating and shielding electrodes will be at ground potential when the deposition is complete. The amount of powder to be deposited can, therefore, be controlled by controlling the bias potential, and it is unrelated to the duration of deposition, once the limit has been reached.

The shielding electrodes and the lower conductive layer can be referred to as the "bias electrodes".

The floating electrodes of the charge imaging chuck determine the pattern of deposition of the medicament powder on the substrate, and hold the powder thereon, During the deposition of powder, the charge imaging chuck is electrically connected to a power source, which is subsequently disconnected after deposition. The floating electrodes can be configured, for example, to spatially determine individual dosages on the inhaler substrate. For example, the conductive layer 100 of the substrate 101 illustrated in FIG. 1 can be a charge imaging chuck. The conductive layer of this chuck can also be used for the electronically assisted release of powder according to the present invention.

Figure 1A:
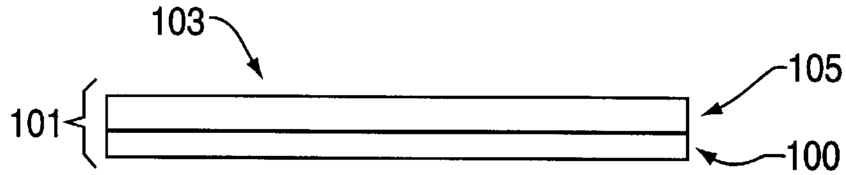
FIGS. 1A and B are a diagrammatic cross-section of one embodiment of a substrate having medicament deposited thereon, the substrate being configured for electronically assisted release of the medicament.
Figure 1B:
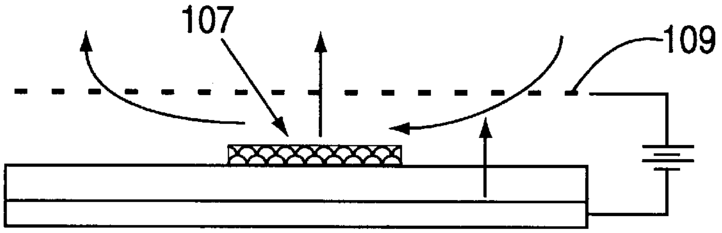

Specifically, FIGS. 1A and B are a diagrammatic cross-section of a substrate 101 having medicament deposited thereon, the substrate having a conductive layer 100 and a dielectric layer 105. The surface 103 of the substrate 101 in contact with medicament 107 is preferably modified according to co-pending application, filed simultaneously herewith, entitled "Inhaler Apparatus with Modified Surface for Enhanced Release of Dry Powders." During assisted release, a conductive layer 109, illustrated as a mesh, is positioned above the substrate and a voltage is applied across these two conductive layers, as shown in FIG. 1B.

Thus, according to one aspect of the present invention, upon inhalation by a patient, the powder is released from the inhaler using an electronic mechanism to assist release. Preferably, the conductive material in the substrate is subjected to an electric pulse.

In certain preferred embodiments, such as when the substrate is solid, in order to release the medicament from the substrate of the inhaler, a potential is applied to the conductive layer in the chuck. Preferably, a conductive material, such as a mesh, is placed above the substrate during release, without having contact with the substrate, and an electric potential is applied between the substrate and the mesh. See, for example, FIG. 1B.

A high voltage pulse is applied across the mesh and the conductive layer in the substrate to trigger release. Preferably, the pulse is synchronized with and triggered by air flow due to inhalation. For example, the inhaler preferably has a switch that activates the pulse upon air flow due to inhalation. The activation is preferably a pulse having a duration of about 300 microseconds to about 1 millisecond. The voltage used is preferably from about 500 to about 2000 volts.

The substrate can alternatively include a conductive layer that is not a charge imaging chuck. For example, the substrate may have a conductive layer with multiple holes, forming a mesh. For release, a second conductive layer having holes therein can be placed above and below the substrate, without having contact with the substrate. An electrical connection between the two conductive layers above and below the substrate provides for electronically assisted release of the powder from the substrate. See, for example, FIG. 2. Preferably, a conductive layer placed above or below the substrate is located from about 1 mm to about 2 mm from the substrate. During release, a high voltage pulse is applied across the two conductive meshes. Preferably, the pulse is synchronized with and triggered by air flow due to inhalation.

Figure 2A:
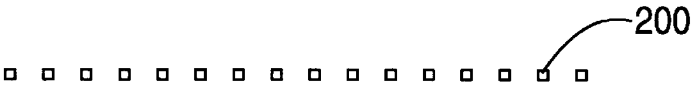
FIGS. 2A and B are a diagrammatic cross-section of another embodiment of a substrate having medicament deposited thereon, the substrate being configured for electronically assisted release of the medicament.
Figure 2B:
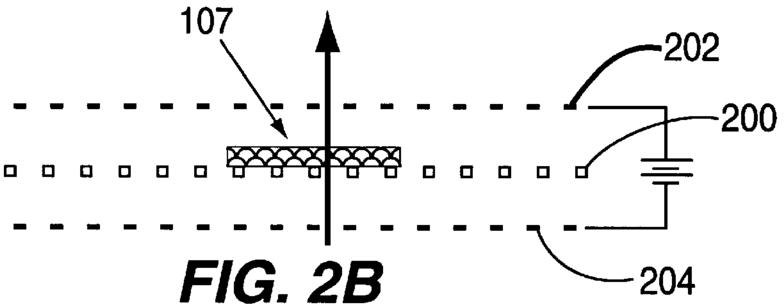

FIGS. 2A and B are a diagrammatic cross-section of a substrate 200 having medicament 107 deposited thereon, the substrate 200 being a mesh. During assisted release, two conductive layers 202 and 204, illustrated as meshes, with holes therein, are positioned above and below the substrate and a voltage is applied across these two conductive layers, as shown in FIG. 2B. When the substrate has holes therein, two conductive layers, one above and one below the substrate, are preferably used to release the medicament from the substrate. Without being limited to a particular theory, it is believed that the use of the two conductive layers with a potential applied across them, enhances the release of powder from the substrates with holes therein in an upward direction, toward the mouthpiece. Preferably, the thickness of the substrate is about 1 mil to about 30 mils.

When the conductive material of the substrate has holes therein, such as a mesh, the holes are preferably configured to maximize air flow so that a substantial amount of the powder is released, and in preferred embodiments, are from about 600 microns to about 2 millimeters in diameter. Preferably, the mesh is made of a metal, such as stainless steel, and the mesh is preferably coated with a dielectric, such as polytetrafluoroethylene ("TEFLON"). The mesh can be a part of the mouthpiece, for example, and is preferably aligned with a single dose prior to inhalation.

Alternatively, for example, the substrate of the inhaler, upon which the medicament is located, can have embedded therein a solid conductive material For example. the substrate may have embedded therein a wire or multiple wires. Preferably, the conductive material is a metal.

Figure 3:
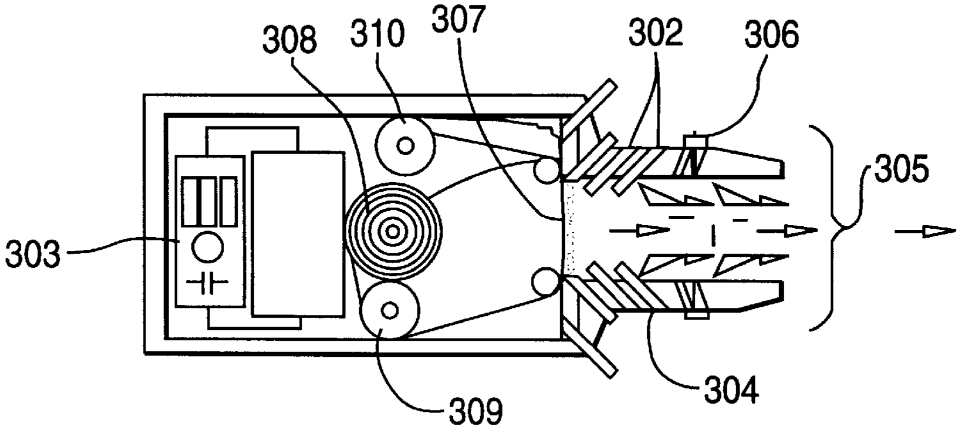
FIG. 3 is a diagrammatic illustration of an embodiment of the inhaler apparatus of the invention having an electronic release mechanism (not shown) powered by a battery.

The power source for the electronic assistance is shown in the context of an exemplary inhaler in FIG. 3, which is a diagrammatic illustration of an embodiment of the inhaler apparatus of the invention having an electronic release mechanism (not shown) powered by a battery 303. In this embodiment, multiple air inlets 302 have channels 304 connected to each inlet to increase release of the powder from the mouthpiece 305. A shuttering mechanism 306 is provided for several of the air inlets 302. The mouthpiece 305 is in air flow communication with the substrate 307 having medicant deposited thereon (not shown). The substrate 307 is in the form of an elongated tape, which is provided by reel 308 and taken up by reel 309. The substrate has a seal (not shown) which is taken up by reel 310.

The electronic assistance of release can be combined with other mechanisms for promoting release, including but not limited to the use of a substrate having grooved indentations to reduce the amount of surface area of the substrate in contact with the powder particles. Preferably, the substrate is modified as described in co-pending application entitled "Inhaler Apparatus with a Modified Surfaces for Enhanced Release of Dry Powders," which has been filed simultaneously herewith and is hereby incorporated by reference herein in its entirety.

It will be understood by those skilled in the art that the inhalers of the invention can be used with numerous types of medicaments, and in addition to oral administration, the inhalers of the invention can be used for nasal administration.

We claim:

1. An inhaler apparatus comprising:

(a) a substrate with electrostatically charged particles of material to be inhaled deposited thereon, said substrate comprising a first conductive layer and a dielectric layer thereon wherein the particles are electrostatically deposited on the dielectric layer and the thickness of the dielectric layer is selected to allow particle retention effective charge image force to be induced between the charged particles and the conductive layer.

2. The inhaler apparatus of claim 1 further comprising:

(b) an electronic release mechanism comprising a voltage source that can be connected to the conductive layer to apply a force on the particles that favors release of the charged particles from the substrate.

3. The inhaler apparatus of claim 1, wherein the conductive layer comprises at least one wire embedded in the substrate.

4. The inhaler apparatus of claim 1, wherein the conductive layer comprises at least one floating electrode that can be biased to attract the charged particles by applying potentials to adjacent electrodes.

5. The inhaler apparatus of claim 4, wherein particles of medicament are electrostatically deposited on the dielectric layer in a pattern determined by the locations of the floating electrodes.

6. The inhaler apparatus of claim 2, wherein the electronic release mechanism further comprises a second conductive layer positioned above the substrate without having contact with the substrate, wherein the voltage source can be connected to the second conductive layer and the conductive layer of the substrate to apply force on the particles that favors release of the charged particles from the substrate.

7. The inhaler apparatus of claim 6, wherein the second conductive layer has openings therein, of dimensions selected to facilitate air and the particle flow through the second conductive layer.

8. The inhaler apparatus of claim 7, wherein the openings of the second conductive layer have a diameter of about 1.5 times the average diameter of the particles.

9. The inhaler apparatus of claim 1 further comprising an electronic release mechansim comprising a second conductive layer positioned above the substrate without having contact with the substrate and a third conductive layer positioned below the substrate.

10. The inhaler apparatus of claim 9, wherein the electronic release mechanism comprises a voltage source that can be connected to the second conductive layer above the substrate and the third conductive layer below the substrate to apply force on the particles that favors release of the particles from the substrate.

11. The inhaler apparatus of claim 1, wherein the first conductive layer in the substrate has openings therein of dimensions selected to facilitate air flow through the first conductive layer.

12. The inhaler apparatus of claim 11, further comprising a second conductive layer positioned above the substrate wherein the openings in the first conductive layer in the substrate have a diameter approximately equal to a diameter of openings in the second conductive layer above the substrate.

13. The inhaler apparatus of claim 12, wherein the openings of the second conductive layer have a diameter of about 1.5 times the average diameter of the particles.

14. The inhaler apparatus of claim 1, wherein the dielectric layer has a textured surface on which the charged particles are deposited, which textured surface has indentations or raised areas defining valleys thereon of dimensions and spacings selected to reduce the amount of the charged particles that can contact a smooth portion of the textured surface.

15. The inhaler apparatus of claim 14, wherein the indentations or valleys have a diameter that is about 5% to about 20% smaller than a minimum selected particle size to be administered by the apparatus.

16. The inhaler apparatus of claim 4 further comprising bias electrodes for inducing a charged particle retentive force at the floating electrode.

17. A method for dispensing a medicament from an inhaler, comprising:

(a) providing an inhaler with a substrate having medicament deposited on a top layer thereof and an electronic release mechanism comprising a first conductive layer positioned underneath the substrate, a second conductive layer positioned above the substrate and a voltage source connected to said first and second conductive layer; and (b) actuating the voltage source to apply a medicament release enhancing electrostatic force on the medicament.

18. The method of claim 17, comprising actuating the voltage source substantially simultaneously with the initiation of an air flow.

19. The method of claim 17, wherein the actuation is a pulse having a duration of about 300 microseconds to about 1 millisecond.

20. The method of claim 17, wherein the voltage is from about 500 to about 2000 volts.

21. An inhaler apparatus comprising:

(a) a substrate with electrostatically charged particles of material to be inhaled deposited to a top surface thereof, and (b) an electronic release mechanism comprising a first conductive layer situated below the substrate, a second conductive layer positioned above the substrate without having contact with the substrate and a voltage source connected to the first and second conductive layers, wherein the voltage source can be activated to apply a force on the particles that favors release from the substrate.

22. The inhaler apparatus of claim 21, wherein the top surface is textured, which textured surface has indentations or raised areas defining valleys thereon of dimensions and spacings selected to reduce the amount of the charged particles that can contact a smooth portion of the textured surface.

23. The inhaler apparatus of claim 22, wherein the indentations or valleys have a diameter that is about 5% to about 20% smaller than a minimum selected particle size to be administered by the apparatus.

24. The inhaler apparatus of claim 21, wherein the second conductive layer has openings therein of dimensions selected to facilitate air and particle flow through the second conductive layer.

25. An inhaler substrate comprising at least one floating electrode and an overlaying dielectric layer, wherein electrostatically charged particles of material to be inhaled can be electrostatically deposited on the dielectric layer in response to an electrostatic force generated at the floating electrode.

26. An inhaler apparatus comprising the inhaler substrate of claim 25 and charged medicament particles deposited on the dielectric layer.

27. The inhaler substrate of claim 25, wherein the dielectric layer has a textured surface on which the charged particles are deposited, which textured surface has indentations or raised areas defining valleys thereon of dimensions and spacings selected to reduce the amount of the charged particles that can contact a smooth portion of the textured surface.

28. The inhaler substrate of claim 27, wherein the indentations or valleys have a diameter that is about 5% to about 20% smaller than a minimum selected particle size to be administered by the apparatus.

* * * * *